United States Patent [19]

Bischoff

[11] Patent Number: Plant 6,099

[45] Date of Patent: Feb. 9, 1988

[54] MINIATURE ROSE PLANT NAMED BISMAR

[75] Inventor: Francis J. Bischoff, Indianapolis, Ind.

[73] Assignee: John C. Walter, Grand Saline, Tex.

[21] Appl. No.: 814,387

[22] Filed: Dec. 30, 1985

[51] Int. Cl.[4] ..... A01H 5/00

[52] U.S. Cl. ..... Plt./7

[58] Field of Search ..... Plt. 7

*Primary Examiner*—Robert E. Bagwill

[57] ABSTRACT

A new and distinct variety of miniature rose plant characterized by (1) bright coral pink buds and blooms with pale pink satiny reverse and (2) a vigorous, compact plant with abundant glossy green foliage.

1 Drawing Figure

The present invention relates to a new and distinct variety of rose plant of the miniature rose class, which was originated by my crossing as seed parent the floribunda rose known as "Little Darling", (U.S. Plant Pat. No. 2,909 expired) and a miniature rose "unknown seedling" as pollen parent.

Among the novel characteristics possessed by this new variety which distinguish it from its parents and all other varieties of which I am aware are: (1) high-centered blooms of bright coral pink with pale pink satiny reverse coloring, (2) an abundance of blooms with flowers borne singly, and often several to a stem in a loose cluster, (3) a pleasant fruity fragrance, (4) a well proportioned plant which is vigorous and shows off its blooms well against its green glossy foliage, and (5) a plant which grows well both in the greenhouse and outdoors, is good for growing in pots, and provides excellent garden decoration as well as cut flowers.

The present variety of miniature rose was originated by me in Marion County, Ind. Carefully controlled conditions and asexual reproduction by cuttings of the new variety as performed by me in Marion County, Ind. show that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonable possible to make the same in a color illustration of this character.

The following is a detailed description of my new rose variety, with color terminology in accordance with The Royal Horticultural Society Colour Chart (RHSCC) except where common dictionary terms of color definition are employed.

Type: Hardy, dwarf, bushy, upright, seedling, greenhouse, outdoors, cut flowers, garden decoration, potted plant.

Class: Miniature.

International identifications:

*Variety.*—Bismar.

*Commercial synonym.*—Marty's Triumph.

THE FLOWER

Observations were made from specimens grown outdoors at Marion County, Ind., U.S.A. in October 1985.

Type: Miniature.

Blooming habit: Recurrent.

Bud:

*Size.*—Medium for miniature.

*Form.*—Pear shaped.

Color:

*When sepals first divide.*—Pale whitish pink (36D), coral point (37C).

*When petals begin to unfurl.*—Inside: Bright coral pink (41C). Outside: Off white (36D and 11D blend).

*When half-blown.*—Inside: Bright coral pink (41C and D), near white hinge (36D). Reverse side of petals: Pale pink blend (36D with 36A,B,C).

Sepals: As long as the bud, thin, pointed, ovate acuminate.

Peduncle: Average length 1", hairy (reddish), erect and stable, green color.

Bloom:

*Size.*—1½" to 1¾" when fully expanded.

*Borne.*—Singly and in sprays of 3 to 7 blooms.

*Form.*—High centered at first, opening to a rather flat bloom.

*Petalage.*—About 30.

*Color.*—During first two days: Inner petals at center of flower: Bright coral pink (41C and 41D). Outer petals: Coral pink (37C). Base of petals (point of attachment): Pale Yellow (11-D). Reverse of petals: Pale pink (blending of 36A,B,C,D). General tonality from a distance: Coral pink (41D).

*Color change.*—Coral pink lightens (39C and D). General tonality: Soft coral pink (39C). After three or more days: Begins to show an almost white center (36D).

Petals:

*Texture.*—Thick.

*Appearance.*—Inside: slightly velvety; Outside: satiny.

*Form.*—Oval — becomes quilled — abrupt, and point at apex.

*Arrangement.*—Regularly arranged.

*Petaloids in center.*—Very few.

*Persistence.*—Whole bloom and peduncle fall off when spent.

*Fragrance.*—Slight fruity fragrance.

*Lasting quality.*—Slow opening on plant, keeps long in refrigerator, good as cut flower.

REPRODUCTIVE ORGANS

Stamens, filaments and anthers:

*Arrangement.*—Bunched tightly around styles.

(Continued on next page.)

*Color.*—Yellow.
Pollen: Yellow.
Styles: Even 3/16" length, thin, tightly bunched.
Stigmas:
*Color.*—Pale green.
Hips:
*Shape.*—Round.
*Size.*—⅜" diameter.
*Color.*—Orange-red when mature.
*Seeds.*—Do not protrude.

PLANT

Form: Upright and compact.
Growth: Vigorous and uniform branching.
*Height attained.*—15 to 18".
Foliage: Mostly 5 leaflets.
*Size.*—Medium for miniature.
*Quantity.*—Abundant.
*Color.*—New foliage: upper side: Glossy Green. under side: Glossy green, slightly lighter. Old foliage: upper side: Dark semi-glossy green. under side: Flat green.
*Shape.*—Oval, pointed.
*Texture.*—Upper side: smooth, healthy appearance. Under side: raised veins.
*Edge.*—Serrated.
*Serration.*—Uniform indentations.
*Leaf stem.*—Color: green, under side: paler green.

*Stipules.*—Medium, ½" pointed.
*Disease resistance.*—Blackspot, good; Mildew, good; Rust, good.
Wood:
*New wood.*—Color: green, Bark: smooth.
*Old wood.*—Color: green, Bark: smooth.
Thorns:
*Quantity.*—Several on main cane, with few on laterals.
*Form.*—Needle shaped with expanded base.
*Length.*—Medium — ⅜" to ½".
*Color when young.*—Pale green.
*Position.*—Irregular.
Prickles:
*Quantity.*—Very few on main canes or on laterals.
Winter hardiness: Needs some protection at 10° or lower. Can use a mound of dirt or leaves.

I claim:

1. A new and distinct variety of rose plant of the miniature rose class, substantially as herein shown and described, characterized particularly by high-centered blooms of bright coral pink with pale pink satiny reverse coloring, with firm, thick petals, borne freely on an upright, bushy plant with glossy green new foliage and semi-glossy darker green old foliage, said plant being easy to propagate from cuttings, and said blooms being long-lasting both on the plant and as cut flowers.

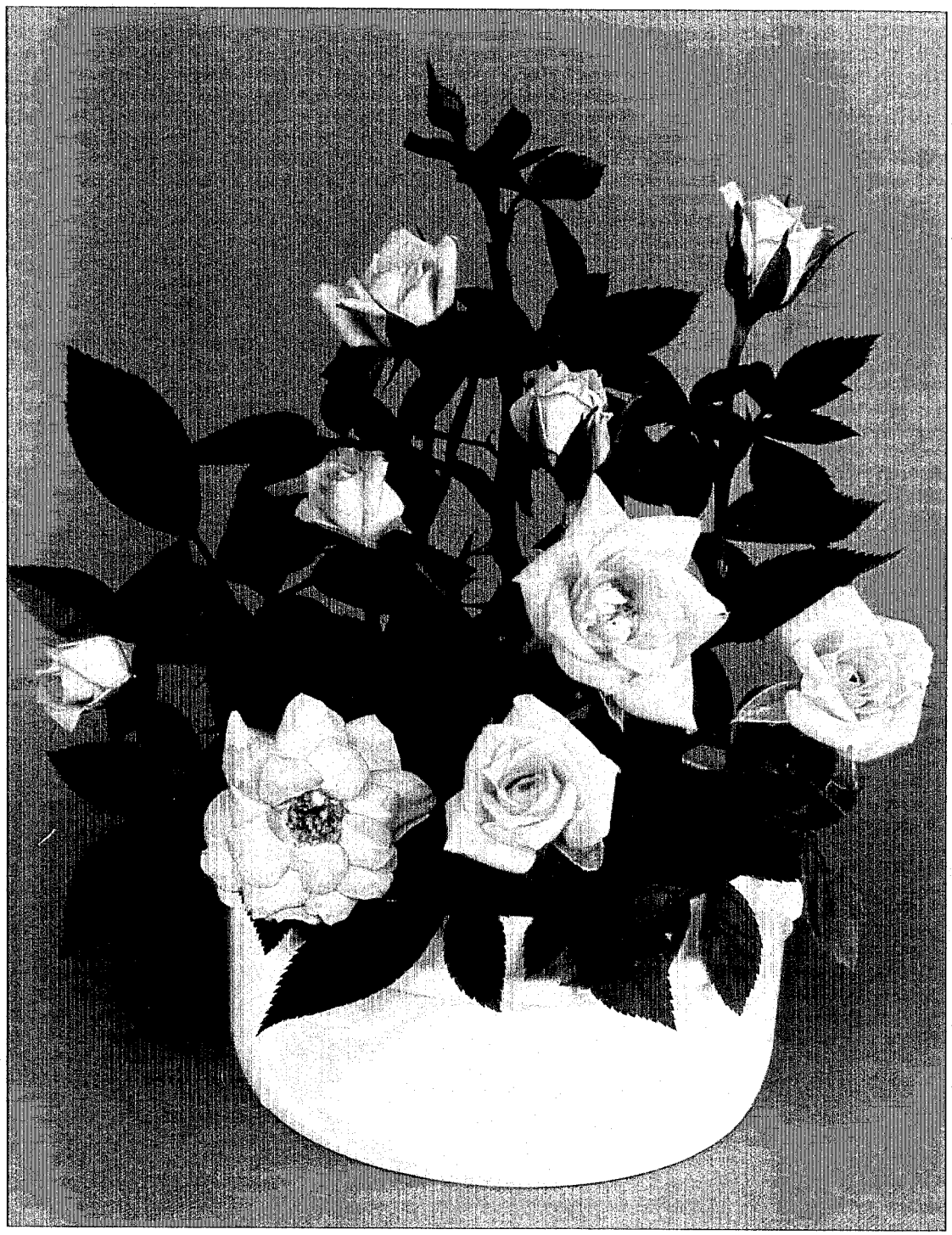

* * * * *